(12) United States Patent
Jacquier

(10) Patent No.: US 6,337,066 B1
(45) Date of Patent: *Jan. 8, 2002

(54) COSMETIC AND/OR DERMATOLOGICAL COMPOSITION BASED ON ASCORBIC ACID IN POWDER FORM

(75) Inventor: Isabelle Jacquier, Paris (FR)

(73) Assignee: L'Oreal, Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/201,090

(22) Filed: Nov. 30, 1998

(30) Foreign Application Priority Data

Dec. 15, 1997 (FR) ............................................ 97 15860

(51) Int. Cl.⁷ ............................................... A61K 7/035
(52) U.S. Cl. ........................................ 424/69; 514/844
(58) Field of Search .......................... 424/69, 499, 500; 514/474, 844

(56) References Cited

U.S. PATENT DOCUMENTS 3,655,406 A * 4/1972 Klaui .......................... 99/148
4,913,896 A    4/1990 Harvey ......................... 424/69
5,439,682 A * 8/1995 Wivell et al. ................ 424/401
5,472,688 A   12/1995 Soukup ....................... 424/70.1

FOREIGN PATENT DOCUMENTS

JP    01 079 105 A    3/1989
JP    02 169 508 A    6/1990

* cited by examiner

*Primary Examiner*—Diana Dudash
*Assistant Examiner*—Alysia Berman
(74) *Attorney, Agent, or Firm*—Oblon, Spivak, McClelland, Maier & Neustadt, P.C.

(57) ABSTRACT

A cosmetic and/or dermatological composition in the form of a powder containing pulverulent ascorbic acid, starch and at least one anionic surfactant. In a preferred embodiment, the composition also contains a water-soluble polymer. The inventive powder composition has good foaming properties when it is moistened with water, and it is useful in particular for cleansing and/or treating the skin. The composition according to the invention is preferably contained in a sponge which is moistened with water and applied directly to the skin.

23 Claims, No Drawings

COSMETIC AND/OR DERMATOLOGICAL COMPOSITION BASED ON ASCORBIC ACID IN POWDER FORM

BACKGROUND OF THE INVENTION

1. Field of the Invention

The invention relates to a cosmetic and/or dermatological composition in the form of a powder containing pulverulent ascorbic acid, a starch and at least one anionic surfactant. This composition is useful, for example, for cleansing the skin, both of the body and of the face, including the area around the eyes and the scalp. The invention also relates to a use of this composition for cleansing and/or treating the skin, as well as to a cosmetic process for cleansing and/or treating the skin.

2. Description of the Background

It has been sought for a long time to formulate ascorbic acid, or vitamin C, in the cosmetic and dermatological fields in different pharmaceutical forms, on account of its many beneficial properties. In particular, ascorbic acid stimulates the synthesis of connective tissue and especially of collagen, it reinforces the skin tissue defences against external attacking factors such as ultraviolet radiation and pollution, it compensates for a vitamin E deficiency in the skin, it depigments the skin, and it has an anti-free-radical activity.

Unfortunately, on account of its chemical structure (an α-keto lactone), ascorbic acid is very sensitive to certain environmental parameters such as light, oxygen and water. This results in rapid degradation of the formulated ascorbic acid when it is in contact with one of these parameters, which is counter to the desired efficacy for treating skin. Moreover, in order to make use of the beneficial effects of ascorbic acid in a skin cleansing composition, it is also necessary for the composition containing it to have good foaming properties without destabilization of the ascorbic acid.

Several solutions have already been envisaged to reduce and/or delay the degradation of ascorbic acid. One of the solutions consists in particular in using ascorbic acid in powder form and in dissolving it in water immediately before use. JP-A-01-079,105 describes a powder based on ascorbic acid for topical application. However, on account of the high acidity of the solution obtained, it is corrosive and runs the risk of causing serious skin irritation. In addition, such a composition has no foaming properties.

There is thus still a need for a composition containing ascorbic acid, which can be stored for several years before being used, while at the same time having good foaming properties when used.

SUMMARY OF THE INVENTION

The inventor has now found a cosmetic and/or dermatological composition which overcomes the drawbacks of compositions containing ascorbic acid described above.

Accordingly, it is an object of the present invention to provide a composition suitable for cosmetic and/or dermatologic use, containing:

pulverulent ascorbic acid, a starch, and at least one anionic surfactant, where the composition is in the form of a powder.

It is another object to providing a method of treating skin by applying the inventive composition to the skin.

A more complete appreciation of the invention and many of the attendant advantages thereof will be readily obtained as the same becomes better understood by reference to the following detailed description.

DETAILED DESCRIPTION OF THE INVENTION

The inventive composition is in the form of a powder, i.e. in the form of a solid finely divided into particles with an average particle size ranging, for example, from 50 to 600 μm and preferably from 150 to 400 μm. These particle sizes include all specific values and subranges therebetween, including 75, 100, 125, 175, 200, 250, 300 and 350 μm.

The powder obtained is prepared by simple mixing of the pulverulent constituents; it is thus easy to manufacture. In addition, it has excellent solubility in water and good foaming properties. Moreover, it is pleasant to use on the skin on account of its softness.

As will be recognized by one skilled in the art, the inventive composition may contain small amounts of water, as long as the composition retains its powder form.

The pulverulent ascorbic acid sold by, for example, Hoffmann-La Roche can be used, as the pulverulent ascorbic acid. The ascorbic acid is present in the composition of the invention in an amount ranging, for example, from 0.1 to 20%, and preferably from 0.5 to 10%, of the total weight of the composition. These ranges include all specific values and subranges therebetween, including 1, 2, 3, 5, 8, 12, 15 and 18% by weight of the total composition.

The nature of the starch in the inventive composition may vary widely. The starch may be, for example, from rice starch, corn starch, wheat starch, potato starch, oat starch, tapioca starch and mixtures thereof. It may be natural or modified.

According to a preferred embodiment of the invention, the starch is a modified starch, and, in particular, a crosslinked starch. This modified starch can be selected, for example, from starches crosslinked with a functional group, for example starches crosslinked with octenylsuccinic anhydride and more particularly "aluminium starch octenyl succinate", such as the product sold by National Starch under the name Dry-Flo, or the crosslinked corn starch sold under the name Resistamyl E2 by Amylum; starches modified in terms of the amylose/amylopectin ratio, such as the product Hylon VII sold by Amylum; modified starches such as the weakly quaternized corn starch sold under the name Myplus W7 by Amylum, the potato starch sold under the name Supramyl P 60 by Amylum, or the hydroxypropyl corn starch sold under the name Merigel EF6 by Amylum.

The starch is present in the composition in an amount which can vary over a wide range. Thus, this amount can range, for example, preferably from 10 to 90%, and more particularly from 30 to 60%, of the total weight of the composition. These ranges include all specific values and subranges therebetween, such as 15, 20, 25, 35, 40, 50, 70, 75, 80 and 85% by weight.

The nature of the anionic surfactant used in the composition according to the invention may vary widely in the context of the present invention. Thus, as examples of anionic surfactants which can be used, alone or as mixtures, in the context of the present invention, mention may be made in particular of salts (particularly alkaline salts, especially sodium salts, ammonium salts, amine salts, amino alcohol salts or magnesium salts) of the following compounds: alkyl sulphates, alkyl ether sulphates, alkylamido ether sulphates, alkylarylpolyether sulphates, monoglyceride sulphates, alkyl sulphonates, alkyl phosphates, alkylamide sulphonates, alkylaryl sulphonates, α-olefin sulphonates, paraffin sulphonates, alkyl sulphosuccinates, alkyl ether sulphosuccinates, alkylamide sulphosuccinates, alkyl sulphosuccinamates, alkyl sulphoacetates, alkyl ether phosphates, acyl sarcosinates, acyl isethionates and N-acyl taurates, the alkyl or acyl radical of these various compounds preferably containing from 12 to 20 carbon atoms, and the aryl radical preferably denoting a phenyl or benzyl group.

Among the anionic surfactants which can also be used, mention may also be made of fatty acid salts such as oleic, ricinoleic, palmitic and stearic acid salts and salts of coconut oil or of hydrogenated coconut oil; acyl lactylates in which the acyl radical contains 8 to 20 carbon atoms.

Among these anionic surfactants, it is more particularly preferred to use isethionate salts such as sodium cocoyl isethionate; glutamate salts such as sodium lauroyl glutamate and the product sold under the name "Amisoft HS-11" by Ajinomoto (CTFA name: "sodium hydrogenated tallow glutamate); sarcosinate salts such as the stearoyl sarcosinate/myristyl sarcosinate mixture; alkyl sulphate salts such as sodium lauryl sulphate and its derivatives; alkyl ether sulphate salts such as sodium laureth sulphate; sulphosuccinate salts such as disodium laureth sulphosuccinate and disodium MEA sulphosuccinate; taurate salts such as sodium methyl cocoyl taurate; α-olefin sulphonate salts such as sodium $C_{14}$–$C_{17}$ sec-alkyl sulphonate; alaninate salts such as sodium lauroyl methylaminopropionate; sodium lauryl sulphoacetate, as well as mixtures thereof.

Other anionic surfactants which may be used in the inventive composition are described in *International Cosmetic Ingredient Dictionary and Handbook,* Volume 2, Seventh Edition, 1997, pp. 1673–1690, incorporated herein by reference.

The anionic surfactant is present in the composition according to the invention in an amount which can vary within a wide range. Thus, this amount can range, for example, from 10 to 80%, and preferably from 30 to 50%, of the total weight of the composition. These ranges include specific values and subranges therebetween, such as 15, 20, 25, 35, 40, 60, 70 and 75% by weight.

According to one specific embodiment of the invention, the composition also comprises at least one water-soluble polymer. This water-soluble polymer can be selected in, particular, from polysaccharides, synthetic polymers, celluloses and clays.

As examples of water-soluble polymers which can be used in the invention, mention may be made of guar gum, xanthan gum, carrageenan gum, cellulose gum or sclerotium gum, derivatives of these gums, hydroxyalkylcelluloses, sodium carboxycelluloses, polyacrylamides and acrylamide copolymers, gelatin, agar-agar, carboxyvinyl polymers (carbomer), montmorillonite and magnesium aluminium silicate.

The amount of polymer in the composition of the invention can range, for example, from 1 to 5%, and preferably from 2 to 3%, of the total weight of the composition. These ranges include all specific value and subranges therebetween such as 1.5, 2.5 and 3.5% by weight.

The composition of the invention may contain additives other than those mentioned above and which are generally used in the cosmetic and dermatological fields, such as, for example, sequestering agents, fragrances, antioxidants, water-soluble active agents, preserving agents, dyestuffs (such as pigments and hydrophilic dyes) and inorganic and/or organic fillers. These additives can be present in the final composition in an amount of from 0 to 50%, preferably from 0.5 to 20% and even more particularly between 0.5 and 10%, of the total weight of the composition. These ranges include all specific values and subranges therebetween, such as 0.75, 1, 2, 5, 12, 15, 25, 30, 40 and 45% by weight.

Of course, a person skilled in the art will take care to select the optional additives and/or the amounts thereof such that the advantageous properties intrinsically associated with the composition in accordance with the invention are not, or are not substantially, adversely affected by the addition(s) envisaged.

As active agents, mention may be made, for example, of softeners such as allantoin, moisturizers such as glycerol and sugars, enzymes and vitamins, and exfoliants such as polyethylene powders and apricot kernel powder.

As fillers, mention may be made, for example, of talcs or magnesium silicate hydrates, micas or aluminosilicates, clays, kaolin or aluminium silicate hydrate, boron nitrides, and acrylic acid or methacrylic acid polymers and copolymers such as the products sold under the name "Polytrap" by Dow Corning.

The composition of the invention may be prepared by mixing all of the constituents in a homogenizer, after optionally grinding the powders whose particle size is too large.

The composition of the invention advantageously contains a medium which is physiologically acceptable for the skin, mucous membranes, the nails, keratin fibres and/or the hair.

In a highly preferred embodiment, the composition of the invention gives rise to the formation of a mousse in the presence of water and in particular has good efficacy for cleansing the skin and in all the applications of vitamin C, especially for treating the skin and in particular for toning and regenerating it, for treating wrinkles and/or fine lines on the skin, for lightening the complexion, for removing skin pigmentation marks, for combating the harmful effects of UV radiation and/or for reinforcing skin tissues against environmental attacking factors.

Thus, a subject of the present invention is also a cosmetic use of the composition according to the invention for cleansing the skin, for treating the skin and, in particular, for toning and regenerating it, for treating wrinkles and/or fine lines on the skin, for lightening the complexion, for removing skin pigmentation marks, for combating the harmful effects of UV radiation and/or for reinforcing skin tissues against environmental attacking factors.

A subject of the present invention is also a cosmetic process for cleansing and/or treating the skin, which consists in using the composition according to the invention.

In these applications, the inventive composition is contacted with water to moisten the composition, and then the composition is applied to the skin to be treated. The composition may be applied to the subject by, for example, simply rubbing the compositions on the skin by hand.

According to one specific embodiment of the invention, the composition of the invention is incorporated in a sponge in single-dose form. The sponge is moistened with water and is then passed over the face and rinsed.

Having generally described this invention, a further understanding can be obtained by reference to certain specific examples which are provided herein for purposes of illustration only and are not intended to be limiting unless otherwise specified.

EXAMPLES

Examples of compositions in accordance with the invention are given below. The amounts are recited as percentages by weight.

Example 1
Cleansing Composition

| | |
|---|---|
| Sodium hydrogenated tallow glutamate | 11% |
| Sodium cocoyl isethionate | 28% |
| Aluminium starch octenyl succinate | 52.3% |
| Allantoin | 0.2% |
| Acrylates copolymer (Polytrap) | 2% |
| Fragrance | 1.5% |
| Ascorbic acid | 5% |

The composition obtained is in the form of a powder with an average particle size of about 250 µm. The powder is moistened before being applied to the skin, and the skin is then rinsed.

Example 2
Cleansing Composition

| | |
|---|---|
| Ascorbic acid | 5% |
| Xanthan gum | 3% |
| Sodium hydrogenated tallow glutamate | 11% |
| Sodium cocoyl isethionate | 28% |
| Aluminium starch octenyl succinate | 49.3% |
| Allantoin | 0.2% |
| Acrylates copolymer (Polytrap) | 2% |
| Fragrance | 1.5% |

The composition obtained is in the form of a powder with an average particle size of about 250 µm. The powder is moistened before being applied to the skin, and the skin is then rinsed.

Obviously, numerous modifications and variations of the present invention are possible in light of the above teachings. It is therefore to be understood that within the scope of the appended claims, the invention may be practiced otherwise than as specifically described herein.

This application is based on French Patent Application FR 97-15860, filed on Dec. 15, 1997, and incorporated herein by reference in its entirety.

I claim:

1. A storage stable cosmetic or dermatologic composition or both, consisting essentially of
   a) ascorbic acid;
   b) a starch in the amount of about 30 to 60% by wt. based upon the total weight of the composition; and
   c) at least one anionic surfactant;
   wherein the composition is in the form of a powder, and each constituent thereof is in pulverulent form,
   and wherein the anionic surfactant is selected from the group consisting of salts of alkyl sulphates, alkyl ether sulphates, alkylamido ether sulphates, alkylarylpolyether sulphates, monoglyceride sulphates, alkyl sulphonates, alkyl phosphates, alkylamide sulphonates, alkylaryl sulphonates, α-olefin sulphonates, paraffin sulphonates, alkyl sulphosuccinates, alkyl ether sulphosuccinates, alkylamide sulphosuccinates, alkyl sulphosuccinamates, alkyl ether sulphosuccinates, alkyl sulphoacetates, alkyl ether phosphates, acyl sarcosinates, acyl isothionates and N-acyl taurates, fatty acid salts, and mixtures thereof.

2. The composition of claim 1, comprising 0.1% to 20% by weight of the ascorbic acid.

3. The composition of claim 1, comprising 0.5% to 10% by weight of the ascorbic acid.

4. The composition of claim 1, wherein the starch is a crosslinked starch.

5. The composition of claim 4, wherein the modified starch is crosslinked with octenylsuccinic anhydride.

6. The composition of claim 1, wherein the anionic surfactant is selected from the group consisting of sodium cocoyl isethionate, sodium lauroyl glutamate, sodium hydrogenated tallow glutamate, the stearoyl sarcosinate/myristyl sarcosinate mixture; sodium lauryl sulphate, sodium laureth sulphate, disodium laureth sulphosuccinate, disodium monoethanolamine sulphosuccinate, sodium methyl cocoyl taurate, sodium $C_{14}$–$C_{17}$ sec-alkyl sulphonate, sodium lauroyl methylaminopropionate, sodium lauryl sulphoacetate, and mixtures thereof.

7. The composition of claim 1, further consisting essentially of at least one additive selected from the group consisting of sequestering agents, fragrances, antioxidants, water-soluble active agents, preserving agents, dyestuffs and fillers.

8. The composition of claim 1, which is contained in a sponge.

9. The composition of claim 8, which foams when contacted with water.

10. The composition of claim 1, which foams when contacted with water.

11. A method of treating the skin, comprising contacting the skin of a subject with the composition of claim 1.

12. The method of claim 11, wherein skin around the eyes of the subject is treated with the composition.

13. The method of claim 11, wherein the composition is contained in a sponge.

14. The method of claim 11, wherein the composition is contacted with water prior to contact with the skin.

15. A storage stable cosmetic or dermatologic composition or both, consisting essentially of
   a) ascorbic acid;
   b) at least one water-soluble polymer
   c) a starch in the amount of about 30 to 60% by wt. based upon the total weight of the composition; and
   d) at least one anionic surfactant;
   wherein the composition is in the form of a powder, and each constituent thereof is in pulverulent form,
   and wherein the anionic surfactant is selected from the group consisting of salts of alkyl sulphates, alkyl ether sulphates, alkylamido ether sulphates, alkylarylpolyether sulphates, monoglyceride sulphates, alkyl sulphonates, alkyl phosphates, alkylamide sulphonates, allylaryl sulphonates, α-olefin sulphonates, paraffin sulphonates, alkyl sulphosuccinates, alkyl ether sulphosuccinates, alkylamide sulphosuccinates, alkyl sulphosuccinamates, alkyl ether sulphosuccinates, alkyl sulphoacetates, alkyl ether phosphates, acyl sarcosinates, acyl isothionates and N-acyl taurates, fatty acid salts, and mixtures thereof.

16. The composition of claim 15, wherein the water-soluble polymer is selected from the group consisting of polysaccharides, synthetic polymers, celluloses and clays, and mixtures thereof.

17. The composition of claim 16, wherein the water-soluble polymer is selected from the group consisting of guar gum, xanthan gum, carrageenan gum, cellulose gum, sclerotium gum, hydroxyalkylcelluloses, sodium carboxycelluloses, polyacrylamides and acrylamide copolymers, gelatin, agar-agar, carboxyvinyl polymers, montmorillonite and magnesium aluminium silicate, and mixtures thereof.

18. The composition of claim 15, wherein the water-soluble polymer is present in an amount of from 1 to 5% by weight.

19. The composition of claim 15 wherein the water-soluble polymer is present in an amount of from 2 to 3% by weight.

20. A method of treating skin, said treatment being selected from the group consisting of toning and regenerating the skin, treating wrinkles and fine lines on the skin, lightening the complexion of the skin, removing skin pigmentation marks, combating harmful effects of UV radiation, and reinforcing skin tissues against environmental attacking factors, which method comprises a) mixing water and a powder composition consisting essentially of
      i) about 0.1 to 20% by weight of pulverulent ascorbic acid;
      ii) about 30 to 60% by wt. of a starch; and
      iii) at least one anionic surfactant selected from the group consisting of salts of alkyl sulphates, alkyl ether sulphates, alkylamido ether sulphates, alkylarylpolyether sulphates, monoglyceride sulphates, alkyl sulphonates, alkyl phosphates, alkylamide sulphonates, alkylaryl sulphonates, $\alpha$-olefin sulphonates, paraffin sulphonates, alkyl sulphosuccinates, alkyl ether sulphosuccinates, alkylamide sulphosuccinates, alkyl sulphosuccinamates, alkyl sulphoacetates, alkyl ether phosphates, acyl sarcosinates, acyl isothionates and N-acyl taurates, fatty acid salts and mixtures thereof; said water and said composition forming a mousse;

b) contacting the skin of a human in need thereof with said mousse.

21. The method of claim 20, wherein skin around the eyes of the subject is treated with the composition.

22. The method of claim 20, wherein the composition is contained in a sponge.

23. The method of claim 20, wherein the composition is contacted with water prior to contact with the skin.

* * * * *

UNITED STATES PATENT AND TRADEMARK OFFICE
CERTIFICATE OF CORRECTION

| | |
|---|---|
| PATENT NO. | : 6,337,066 B1 |
| DATED | : January 8, 2001 |
| INVENTOR(S) | : Isabelle Jacquier |

Page 1 of 1

It is certified that error appears in the above-identified patent and that said Letters Patent is hereby corrected as shown below:

<u>Column 6,</u>
Line 28, between the words "wherein" and "skin", insert -- the --

Signed and Sealed this

Nineteenth Day of March, 2002

Attest:

JAMES E. ROGAN
*Director of the United States Patent and Trademark Office*

*Attesting Officer*